United States Patent [19]
Volk

[11] Patent Number: 5,963,301
[45] Date of Patent: Oct. 5, 1999

[54] LENSE ARRANGEMENT FOR VITREORETINAL SURGERY

[75] Inventor: Donald A. Volk, Mentor, Ohio

[73] Assignee: Volk Optical, Inc., Mentor, Ohio

[21] Appl. No.: 09/176,801

[22] Filed: Oct. 22, 1998

Related U.S. Application Data

[60] Provisional application No. 60/062,612, Oct. 22, 1997.

[51] Int. Cl.[6] .................................................. A61B 3/00
[52] U.S. Cl. .................................................. 351/219
[58] Field of Search .................................. 351/205, 219, 351/160 R, 246, 247; 606/4, 166

[56] References Cited

U.S. PATENT DOCUMENTS

| | | |
|---|---|---|
| 1,782,331 | 11/1930 | Wilhelm . |
| 4,558,698 | 12/1985 | O'Dell . |
| 4,575,205 | 3/1986 | Rappazzo ................................ 351/219 |
| 5,046,836 | 9/1991 | Volk . |
| 5,347,326 | 9/1994 | Volk . |
| 5,523,810 | 6/1996 | Volk ........................................ 351/219 |
| 5,623,323 | 4/1997 | Johnson et al. . |

OTHER PUBLICATIONS

Ocular Instruments, Inc., Ocular Instruments Product Catalog, 1995, various pages.

Maurice B. Landers III, M.D., et al., The Optics of Vitreous Surgery, 1981, pp. 611–614.

*Primary Examiner*—George Manuel
*Attorney, Agent, or Firm*—Venable; Robert Kinberg

[57] ABSTRACT

A lens arrangement for use in vitreoretinal surgery includes a contact lens element including a posterior surface having a shape adapted to fit an average cornea for placement on a patient's eye and an anterior surface. The contact lens element transmits light emanating from the patient's eye for viewing a structure of the patient's eye. A flange surrounds and holds a peripheral region of the contact lens element and extends radially onto the scleral region of the patient's eye. The flange has a posterior surface with a shape adapted to fit an average scleral curvature so that the flange rests on the sclera for stabilizing a position of the contact lens on the patient's cornea. The flange includes at least one opening allowing access to an incision through which a surgical tool or instrument may be inserted into the eye.

24 Claims, 2 Drawing Sheets

LENSE ARRANGEMENT FOR VITREORETINAL SURGERY

CROSS-REFERENCE TO RELATED APPLICATIONS

This application claims the benefit of the filing date of Provisional Application Ser. No. 60/062,612, filed Oct. 22, 1997, the disclosure of which is incorporated herein by reference.

BACKGROUND OF THE INVENTION

The invention relates to a lens arrangement for observation and surgical treatment of the vitreous or retina of the eye, and more particularly for use in vitreoretinal surgery.

Direct ophthalmoscopy lenses which create a virtual image within the eye and indirect ophthalmoscopy lenses which create a real image outside of the eye are two lens types which have been used for fundus observation and as aids in the surgical treatment of the eye. Known lenses of this type that are used in vitreoretinal surgery are maintained on the eye through the use of a handle that is held by an assistant during the surgery. A problem exists with the use of such a handle in that the assistant may require considerable prior experience in vitreoretinal surgical procedures, and that the exact lens position required may be tiresome as well as difficult to maintain over the course of the surgery, especially if there is some movement of the eye or if some movement of the imaging lens is desired to aid the physician in his work.

It is also known to hold such lenses in place with the use of a suture down ring. The suture down ring is comprised of metal or other bio-compatible material and has one or more extending fingers or leg portions around which sutures, which have been sewn into the sclera, are tied. The lens, which may be, for example, a plano-concave direct ophthalmoscopy lens or an indirect ophthalmoscopy lens system comprised of two or more elements, slips into the suture down ring and is thereby stabilized and centered over the cornea. Commonly, a sterile interface solution is used in conjunction with the lens to produce an optical interface of the lens with the eye. The suture down ring has been successfully used, but because its use involves a suturing procedure it could be desirably avoided were there to be a suitable non-invasive alternative.

SUMMARY OF THE INVENTION

It is an object of the invention to provide a lens arrangement to facilitate vitreoretinal surgery.

It is a further object of the invention to provide a lens arrangement to facilitate vitreoretinal surgery which involves a non-invasive stabilization of an ophthalmoscopy lens on the eye without using a manually held handle.

The above and other objects are accomplished according to the invention by the provision of a lens arrangement for use in vitreoretinal surgery, including a contact lens element having a posterior surface adapted to fit an average cornea for placement on a patient's eye, and an anterior surface, the contact lens element transmitting light emanating from the patient's eye for viewing a structure of the patient's eye; and a flange surrounding and holding a circumferential edge of the contact lens element and extending radially onto the scleral region of the patient's eye, the flange having a posterior surface with a shape allowing it to rest on the scleral portion of the eye for stabilizing a position of the contact lens element on the patient's cornea, the flange having one or more openings allowing access to an incision through which a surgical tool or instruments may be inserted.

In a preferred embodiment the one or more openings comprise a plurality of spaced apart recesses each having an opening at the out peripheral edge of the flange and extending radially inwardly, the opening and inward radial extent of each recess allowing access to an incision through which a surgical tool or instruments may be inserted.

In an alternative embodiment, the stabilizing portions of the flange existing between the one or more openings or recesses may include vacuum suction ports or channels designed to conduct a partial or high vacuum to further enhance the stable positioning of the lens on the eye.

The contact lens element may comprise a direct ophthalmoscopy lens, for example, of the plano-concave, convex-concave or bi-concave type, or alternatively may be part of a multi-element indirect ophthalmoscopy lens. Further, the contact lens element and flange may comprise an integral, one piece unit made of the same material. Alternatively, the flange may comprise a separate component made of the same or different material from the contact lens element. In the latter case the contact lens element may slidably fit within a central opening of the flange or may be releaseably connected by other suitable mechanisms, such as a screw connection friction fit or a bayone connection.

As desired, the various embodiments described may be used without the aid of an assistant's handle, or alternatively may be used in conjunction with such a handle to provide increased control or maneuverability of the lens on the eye.

Other features and advantages of the invention will become apparent from the following detailed description of the invention in conjunction with the accompanying drawings

DETAILED DESCRIPTION OF THE INVENTION

Figure 1:
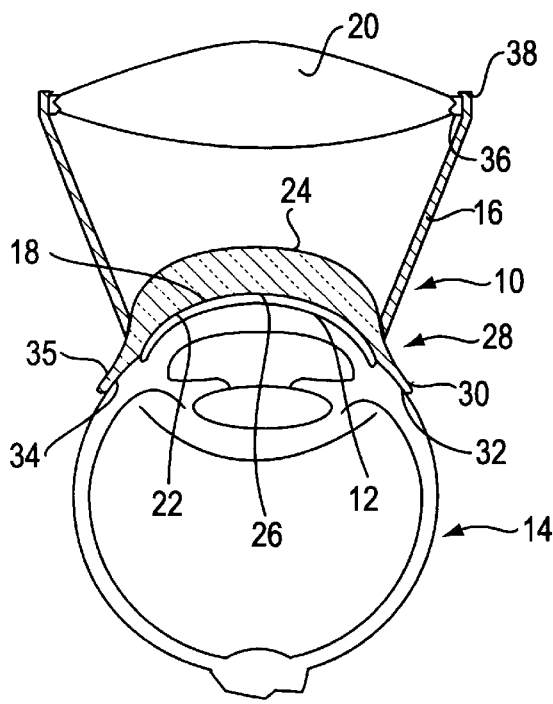
FIG. 1 is a sectional view of a lens arrangement according to one embodiment of the invention.
Figure 2:
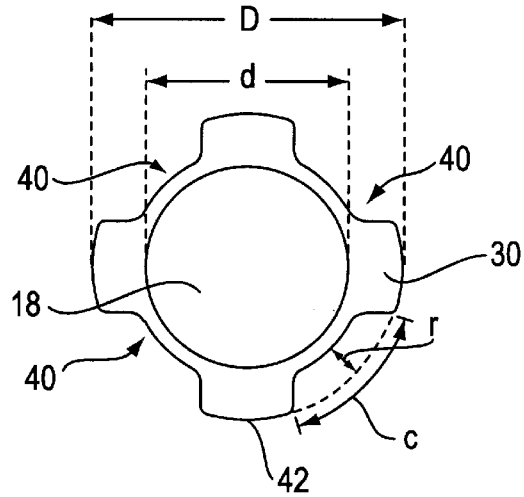
FIG. 2 is a plan view of the contact lens element and flange illustrated in FIG. 1.

Referring to FIG. 1, there is shown a sectional view of a lens arrangement 10 mounted on a cornea 12 of an eye 14. Lens arrangement 10 includes a frusto-conically shaped frame 16 which coaxially fixes a contact lens element 18 relative to an imaging lens 20, which together comprise an indirect ophthalmoscopy contact lens arrangement for creating a real aerial image of a structure in the eye anterior to the cornea of the examined eye. Contact lens element 18 has a concave posterior surface 22 and a convex anterior surface 24. Concave posterior surface 22 has a shape substantially corresponding to the shape of an average cornea and therefore may have an apical radius of approximately 7.0 to 8.5 mm, and preferably may be approximately 7.7 to 7.8 mm. Posterior surface 22 may be spherical or aspherical and may be fitted on the cornea with the use of an interface solution 26 as is commonly known in the art. Referring additionally to FIG. 2, posterior surface 22 preferably has a cord diameter d of approximately 9–13 mm and is most preferably about 11.7 mm. Anterior surface 24 may have an apical radius ranging from infinity for a planar surface to either a convex or concave radius of approximately 6.0 mm., and may be either spherical or aspherical. Contact lens element 18 has a peripheral region 28 which is connected with a flange 30 around its circumference. Flange 30 extends radically onto the sclera 32 of eye 14. Flange 30 has a posterior surface 34 which has a different curvature from that of posterior surface 22 of contact lens element 18, and more specifically, posterior surface 34 of flange 30 has a curvature substantially corresponding to the curvature of an average sclera of an eye, for example, a 12 mm. radius. Consequently, the curvature of the posterior surface 34 of flange 30 is substantially flatter than the curvature of the posterior surface 22 of contact lens element 18, and as such the lens device tends to be stabilized and centered over the cornea of the eye. Flange 30 has an anterior surface 35 that may have a slope or curvature that provides an adequate thickness of approximately 1.5 mm. to flange 30, thereby providing substantiality and strength to this component. Posterior surface 34 of flange 30 has a outside cord diameter D which may range from approximately 15 mm to approximately 20 mm, and is preferably 16 to 17 mm in diameter. Contact lens element 18 is fixed, for example, by a screw connection (not shown) to the smaller diameter end of frusto-conical frame 16. Imaging lens 20 is fixed at the larger opening end of frusto-conical frame 16 between a shoulder 36 and an o-ring 38, or by other conventional fastening means. Imaging lens 20 is coaxially fixed relative to contact lens element 18 and is preferably biconvex with a power which may be as high as 150 to 170 diopters. Imaging lens 20 is spaced from and cooperates in a known manner with contact lens element 18 for capturing light rays exiting the eye through the cornea and passing through contact lens element 18. Imaging lens 20 focuses such light rays to create a real image of the retina and vitreous anterior to the cornea, and preferably anterior of imaging lens 20. An indirect ophthalmoscopy lens system of this type which includes a contact lens element and one or more imaging lenses is known in the art and is described in detail, for example, in my prior U.S. Pat. No. 5,046,836, which is incorporated herein by reference.

FIG. 2 is a plan view of contact lens element 18 and flange 30. In this embodiment, contact lens element 18 and flange 30 are made of the same optically transparent material and are integrally connected with one another in peripheral region 28 as a single unit. As can be seen in FIG. 2, flange 30 has four evenly spaced recesses 40 each of which has an opening at the outer periphery 42 of flange 30 and extend radially inwardly toward contact lens element 18. The circumferential extent C of the opening of each recess 40 at the outer periphery 42 may be from about 4 to about 8 mm, and is preferably about 6.75 mm, and each recess 40 extends radially inwardly from an imaginary extension of the outer periphery 42, shown by a dotted line in FIG. 2 in the lower right-hand recess, by a distance "r" of about 1 to about 5.5 mm, and is preferably about 2.15 mm. In general, the recess or recesses are sized to accommodate known dimensions of current surgical tools which penetrate the sclera during vitreoretinal surgery.

Figure 3:
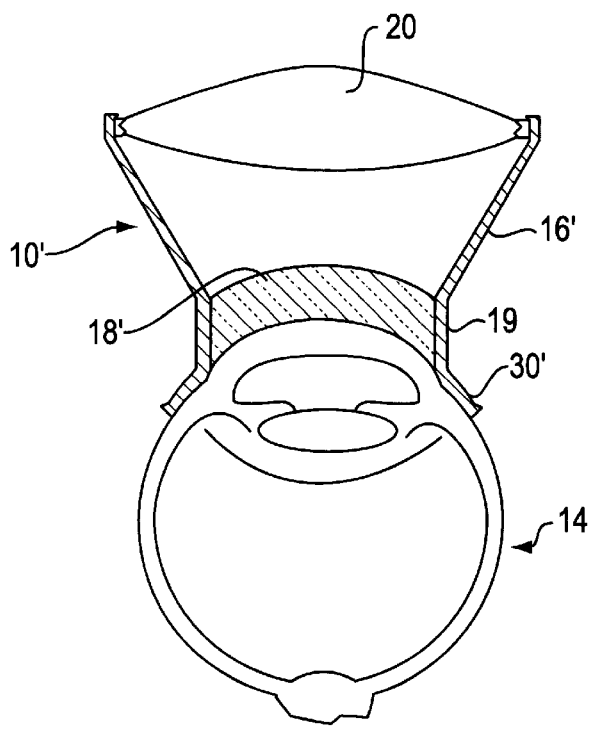
FIG. 3 is a sectional view of a lens arrangement according to another embodiment of the invention.
Figure 4:
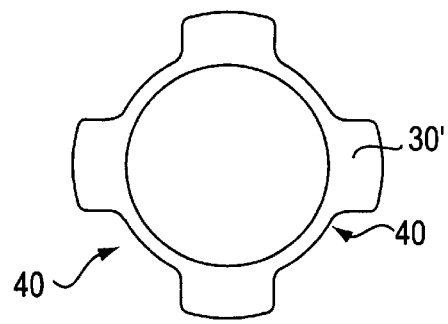
FIG. 4 is a plan view of the flange shown FIG. 3.

FIGS. 3 and 4 illustrate an embodiment modified from that of FIGS. 1 and 2 wherein a flange 30' constitutes a separate component from that of contact lens element 18' which is fixed in frame 16' coaxially with imaging lens 20. Flange 30', which is shown in plan view in FIG. 4, may be made of metal or any other suitable material which is biocompatible with the eye. In this embodiment, contact lens element 18' presents a circumferential edge 19 which has a diameter the same or just slightly less than the inner diameter of flange 30' so that contact lens element 18' can be slidably received within flange 30' for stabilizing the indirect ophthalmoscopy lens system 10' relative to eye 14. Recesses 40 in flange 30' are sized the same as described in connection with FIG. 2. Flange 30' thus operates in the same manner as flange 30 in FIG. 2 to stabilize the lens system 10' relative to the eye. Flange 30' may be designed to accommodate lens types presently used in vitreoretinal surgery, thus providing a means by which such existing lenses may be used advantageously without the need for a handle or suture down ring.

Figure 5:
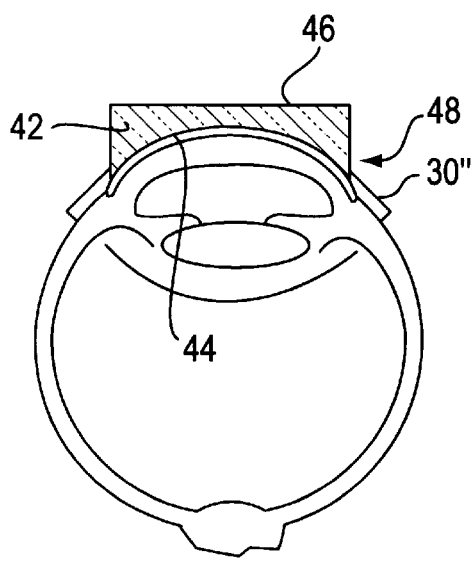
FIG. 5 is a sectional view of a lens arrangement according to yet another embodiment of the invention.

FIG. 5 shows an embodiment of the invention wherein a flange 30" is integrally connected with a direct ophthalmoscopy lens 43. Direct ophthalmoscopy lens 43 has a concave posterior surface 44 which has a shape adapted to fit an average cornea and a plano anterior surface 46. Direct ophthalmoscopy lens 43 operates in a known manner for creating a virtual image of the patient's retina which can be viewed through a microscope by an observer. In accordance with the invention, flange 30", which is connected to direct ophthalmoscopy lens 43 in a peripheral region 48, has 4 recesses like those illustrated in FIG. 2, spaced apart evenly around the circumference of the flange for accommodating surgical tools or instruments inserted into the eye during surgery. Although FIG. 5 illustrates direct ophthalmoscopy lens 43 and flange 30" as constituting a single component made of the same optically transparent material, it is possible for flange 30" and direct ophthalmoscopy lens 43 to be separate components. In such a case, the flange would releaseably receive the direct ophthalmoscopy lens for stabilizing the lens relative to the eye during a surgical or diagnostic procedure much the same as described above in connection with the embodiment of FIGS. 3 and 4.

Figure 6:
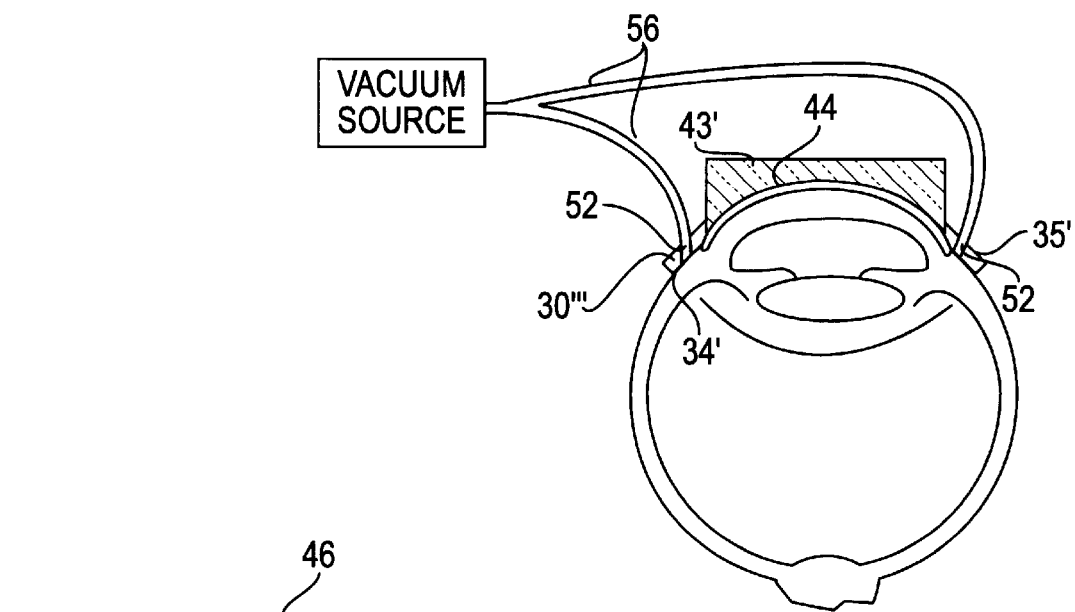
FIG. 6 is a sectional view and partial block diagram of a lens arrangement according to a further embodiment of the invention.
Figure 7:
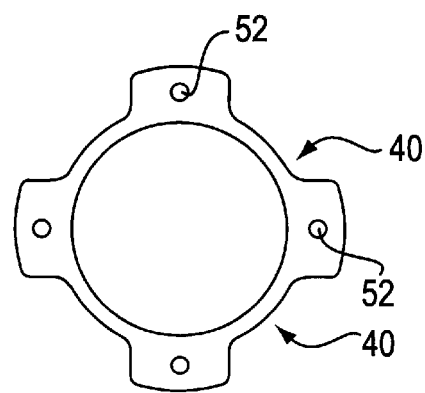
FIG. 7 is a plan view of the flange shown in FIG. 6.

FIGS. 6 and 7 show a contact lens arrangement relating to an embodiment of the invention wherein a flange 30'" incorporates vacuum ports 52 communicating with the posterior surface 34' of the flange to further enhance the stable positioning of a slidably received direct ophthalmoscopy contact lens element 43' through vacuum suction to the sclera of a patient's eye 14. A vacuum port may be located on one or more of the structural portions of the flange between the recesses 40, and may be designed as a channel at the posterior surface or hole passing through the body of the flange from posterior surface 34' to anterior surface 35'. At anterior surface 35' a small diameter flexible hose 56, such as surgical silicone hose, may be adapted to the vacuum ports 52 and connected to a vacuum source 58 such as a metered vacuum pump squeeze bulb or syringe operated by the physician's assistant.

Figure 8:
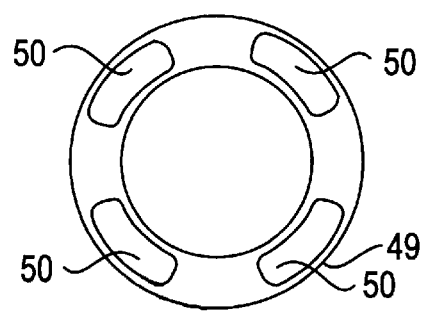
FIG. 8 is a plan view of another embodiment of the flange.

Various modifications may be made to the lens arrangements described above without departing from the spirit and scope of the invention. For example, the flange surrounding the contact lens element may incorporate a bridge 49 to form fully enclosed openings 50 as shown in FIG. 8. In a further modification, bridge 49 may incorporate a vacuum channel extending partly or fully around the circumference of the lens for the same purpose as described in the embodiment of FIGS. 6 and 7. In a further modification the flange may have less than four recesses or openings. Specifically, it is possible for the flange to have one recess, or alternatively three recesses or openings spaced apart at the 11 o'clock, 2 o'clock and 4 or 8 o'clock positions, which are incision positions that a surgeon may typically utilize for inserting surgical tools or instrumentation into the eye during a surgical procedure. Further, the size of the recesses or openings may vary from the dimensions mentioned above, particularly in the circumferential extent of the recess or opening.

It should be apparent that other changes and modifications may be made without departing from the invention in its broader aspects, and the invention, therefore, as defined in the appendant claims is intended to cover all such changes and modifications that fall within the true spirit of the invention.

What is claimed:

1. A lens arrangement for use in vitreoretinal surgery, comprising:
   a contact lens element including a posterior surface having a shape substantially corresponding to a shape of an average cornea for placement on a patient's eye and an anterior surface, the contact lens element transmitting light emanating from the patient's eye for viewing a structure of the patient's eye; and a flange surrounding and holding a peripheral region of the contact lens element and extending radially onto the scleral region of the patient's eye, the flange having a posterior surface adapted to fit an average scleral curvature so that the flange rests on the sclera for stabilizing a position of the contact lens on the patient's cornea, the flange including at least one opening allowing access to an incision through which a surgical tool or instrument may be inserted into the eye.

2. The lens arrangement according to claim 1, wherein the posterior surface of the contact lens element has a diameter of about 10 mm to about 12 mm.

3. The lens arrangement according to claim 1, wherein the flange has an outer diameter of about 15 mm to about 20 mm.

4. The lens arrangement according to claim 1, wherein the flange has an outer periphery and the openings in the flange comprise recesses that open at the outer periphery of the flange and extend radically inwardly, and the recesses each have a circumferential extent at the outer periphery of the flange of about 4 mm to about 8 mm.

5. The lens arrangement according to claim 4, wherein the inward extent of the respective recesses from an imaginary extension of the periphery of the flange at the recess is from about 1 mm to about 5.5 mm.

6. The lens arrangement according to claim 1, wherein the anterior surface of the contact lens element has a shape that is one of plano, convex and concave, and the contact lens element constitutes a direct ophthalmoscopy lens for creating a virtual image of a structure of the patient's eye.

7. The lens arrangement according to claim 1, and further comprising an imaging lens mounted anterior of the contact lens element, the imaging lens capturing and focusing light rays exiting the contact lens for creating a real aerial image of a structure of the patient's eye anterior the patient's eye.

8. The lens arrangement according to claim 7, and further including a frame fixing the imaging lens coaxially with the contact lens element.

9. The lens arrangement according to claim 1, wherein the posterior surface of the contact lens element and the posterior surface of the flange have different curvatures.

10. The lens arrangement according to claim 9, wherein the posterior surface of the contact lens element has a curvature that is steeper than the posterior surface of the flange.

11. The lens arrangement according to claim 1, wherein the at least one opening comprises 3 openings spaced approximately at 11 o'clock, 2 o'clock and 4 or 8 o'clock, positions, respectively.

12. The lens arrangement according to claim 1, wherein the plurality of openings includes at least 4 openings spaced apart approximately equidistantly.

13. The lens arrangement according to claim 1, wherein the flange and the contact lens element comprise an integral one piece unit.

14. The lens arrangement according to claim 1, wherein the flange and the contact lens element are separate components.

15. The lens arrangement according to claim 14, wherein the flange and the contact lens element have a releaseable connection.

16. The lens arrangement according to claim 1, wherein the openings comprise recesses that open onto the outer periphery of the flange.

17. The lens arrangement according to claim 16, wherein the recesses are generally U-shaped.

18. The lens arrangement according to claim 1, wherein the flange includes at least one port for connection to vacuum source to create suction at the posterior side of the flange to aid in a stable positioning of the lens arrangement on a patient's eye.

19. The lens arrangement according to claim 18 in combination with one of a metered vacuum pump squeeze bulb or syringe connected to the at least one port for drawing the vacuum.

20. The lens arrangement according to claim 18 in combination with a syringe connected to the at least one port for drawing the vacuum.

21. A method for stabilizing a lens on a patient's during vitreoretinal surgery, the lens including a contact lens element having a posterior surface with a shape substantially corresponding to a shape of an average cornea for transmitting light emanating from the patient's eye for viewing a structure of the patient's eye, the method comprising the steps of:
   surrounding and holding the contact lens element with a flange extending radially onto the scleral region of the patient's eye, the flange having a posterior surface with a shape corresponding to an average scleral curvature so that the flange rests on the sclera for stabilizing a position of the contact lens on the patient's cornea; and
   providing the flange with at least one opening allowing access to an incision through which a surgical tool or instrument may be inserted into the eye.

22. The method of claim 21, wherein the flange has an anterior surface and the method further includes providing the flange with at least one channel extending between the posterior surface and the anterior surface, and connecting the channel to a vacuum source to create a suction to between the flange and the sclera of the patient's eye.

23. The method of claim 21, and further including providing a releaseable connection between the contact lens element and the surrounding flange.

24. The method of claim 21, further including making the flange and the contact lens element an integral one piece unit.

* * * * *

UNITED STATES PATENT AND TRADEMARK OFFICE
CERTIFICATE OF CORRECTION

| | | Page 1 of 1 |
|---|---|---|
| PATENT NO. | : 5,963,301 | |
| APPLICATION NO. | : 09/176801 | |
| DATED | : October 5, 1999 | |
| INVENTOR(S) | : Donald A. Volk and Kakarla V. Chalam | |

It is certified that error appears in the above-identified patent and that said Letters Patent is hereby corrected as shown below:

Title page, under item (12) delete "Volk" and insert -- Volk et al. --.

Title page, item [75] Inventor: "Donald A. Volk, Mentor, Ohio" should read --Donald A. Volk, Mentor, Ohio and Kakarla V. Chalam, Jacksonville, Florida--.

Signed and Sealed this
Fourteenth Day of February, 2012

David J. Kappos
*Director of the United States Patent and Trademark Office*